US011553852B2

(12) United States Patent
'T Hooft et al.

(10) Patent No.: US 11,553,852 B2
(45) Date of Patent: Jan. 17, 2023

(54) SYSTEM FOR DISTRIBUTED BLOOD FLOW MEASUREMENT

(75) Inventors: Gert Wim 'T Hooft, Eindhoven (NL); Adrien Emmanuel Desjardins, Waterloo (CA); Maya Ella Barley, Walton on Thames (GB); Raymond Chan, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2034 days.

(21) Appl. No.: 14/117,861

(22) PCT Filed: May 29, 2012

(86) PCT No.: PCT/IB2012/052665
§ 371 (c)(1),
(2), (4) Date: Mar. 19, 2014

(87) PCT Pub. No.: WO2012/164481
PCT Pub. Date: Dec. 6, 2012

(65) Prior Publication Data
US 2014/0194757 A1    Jul. 10, 2014

Related U.S. Application Data

(60) Provisional application No. 61/491,946, filed on Jun. 1, 2011.

(51) Int. Cl.
*A61B 5/026* (2006.01)
*A61B 5/028* (2006.01)
(Continued)

(52) U.S. Cl.
CPC ............ *A61B 5/0261* (2013.01); *A61B 5/028* (2013.01); *A61B 5/6852* (2013.01); *G01F 1/6884* (2013.01); *A61B 2562/0233* (2013.01)

(58) Field of Classification Search
None
See application file for complete search history.

(56) References Cited

U.S. PATENT DOCUMENTS 3,915,155 A * 10/1975 Jacobson ............... A61B 5/028
600/505
4,153,048 A * 5/1979 Magrini ............... A61B 5/6857
600/505
(Continued)

FOREIGN PATENT DOCUMENTS

| GB | 2308652 A | 7/1997 |
| GB | 2308888 A | 7/1997 |
| WO | 2004007014 A1 | 1/2004 |

OTHER PUBLICATIONS

"Fibre Optic Hot-Wire Flowmeter based on a Metallic Coated Hybrid LPG-FBG Structure" P. Caldas et al, Proceedings of the European Workshop on Optical Fiber Sensors (Porto, 2010) SPIE vol. 7653, p. 132.

(Continued)

*Primary Examiner* — Michael R Bloch

(57) ABSTRACT

A medical system for minimally-invasive measurement of blood flow in an artery (AT). An interventional device (IVD) with an optical fiber (FB) comprising a plurality of temperature-sensitive optical sensor segments, e.g. Fiber Bragg Gratings, spatially distributed along its longitudinal extension is configured for insertion into an artery (AT). A temperature changer (TC) is arranged in the WD to introduce a local change in temperature ($\Delta T$) of a bolus of blood in the artery, to allow thermal tracking over time with the optical fiber (FB). A measurement unit (MU) with a laser light source (LS) delivers light to the optical fiber (FB) and receives light reflected from the optical fiber (FB) and generates a corresponding time varying output signal. A first algorithm (A1) translates this time varying output signal into (Continued)

a set of temperatures corresponding to temperatures at respective positions along the optical fiber (FB). A second algorithm (A2) calculates a measure of blood flow (BF) at respective positions along the optical fiber (FB) in accordance with a temporal behavior of said set of temperatures. Such system can be used to quickly scan an artery for diagnosing stenotic regions without the need for pullbacks or injection of toxic liquids. A good spatial resolution of the blood flow measurement can be obtained in real-time.

16 Claims, 3 Drawing Sheets

(51) Int. Cl.
*G01F 1/688* (2006.01)
*A61B 5/00* (2006.01)

(56) References Cited

U.S. PATENT DOCUMENTS

| | | | |
|---|---|---|---|
| 4,212,298 A * | 7/1980 | Gezari | A61M 5/20 128/DIG. 12 |
| 4,397,314 A * | 8/1983 | Vaguine | A61B 18/18 374/122 |
| 4,621,929 A * | 11/1986 | Phillips | A61B 5/028 356/44 |
| 4,841,981 A * | 6/1989 | Tanabe | A61B 5/029 600/505 |
| 5,174,299 A | 12/1992 | Nelson | |
| 5,207,227 A | 5/1993 | Powers | |
| 5,509,424 A * | 4/1996 | Al-Ali | A61B 5/028 128/925 |
| 5,526,816 A * | 6/1996 | Arditi | A61B 8/481 600/458 |
| 5,954,659 A * | 9/1999 | Curley | A61B 5/028 600/504 |
| 5,989,192 A * | 11/1999 | Weijand | A61B 5/028 600/504 |
| 6,746,408 B2 * | 6/2004 | Krivitski | A61M 1/3656 600/309 |
| 8,678,642 B2 * | 3/2014 | Jester | G01R 33/285 374/1 |
| 2003/0120148 A1 * | 6/2003 | Pacetti | A61M 25/09 600/421 |
| 2004/0007014 A1 | 1/2004 | Takeuchi et al. | |
| 2006/0028650 A1 | 2/2006 | Crickmore et al. | |
| 2006/0106308 A1 | 5/2006 | Hansmann | |
| 2006/0126073 A1 * | 6/2006 | Farrell | G01B 11/026 356/482 |
| 2006/0235314 A1 | 10/2006 | Migliuolo | |
| 2012/0179390 A1 * | 7/2012 | Kimmiau | E21B 47/001 702/45 |

OTHER PUBLICATIONS

"Measurement of Blood Flow by Thermodilution" Ganz et al, Seminar on Clinical Application of Techniques to Measure Blood Flow in Man. Part 2. vol. 29, Feb. 1972.
"Coronary Pressure Wire" MSAC Application 1080, Assessment Report, Nov. 2005. p. 1-130.

* cited by examiner

SYSTEM FOR DISTRIBUTED BLOOD FLOW MEASUREMENT

CROSS-REFERENCE TO PRIOR APPLICATIONS

This application is the U.S. National Phase application under 35 U.S.C. § 371 of International Application Serial No. PCT/IB2012/052665, filed on May 29, 2012, which claims the benefit of Application Ser. No. 61/491,946, filed on Jun. 1, 2011. These applications are hereby incorporated by reference herein.

FIELD OF THE INVENTION

The present invention relates to the field of medical devices. More specifically, the invention relates to systems and methods for optically measuring of blood flow by minimally-invasive intervention.

BACKGROUND OF THE INVENTION

Accurately measuring blood flow resistance in the vasculature is important for diagnosing and treating stenotic regions, such as for diagnosing stenotic regions e.g. in heart coronary arteries. Stenotic regions in an artery are typically identified with fluoroscopy in conjunction with radio-opaque contrast agents, and their functional impact is quantified with the fractional flow reserve (FFR) method in many different clinical contexts, including in coronary and renal arteries. With FFR, a sensor positioned at the tip of a wire is used to measure pressure, and the FFR is calculated from the ratio of the pressure at the distal and proximal end of the stenosis, and a stenotic region is deemed to require treatment when this ratio is below 0.7 to 0.8. However, both of these methods have disadvantages. Iodinated contrast agents are nephrotoxic and thus especially problematic to use on patients with poor renal function. FFR probes are currently expensive to manufacture and require pullbacks for distributed measurements, thus requiring a rather complicated and time consuming invasive procedure.

An accompanying method to quantify the physiological condition of the coronary system is coronary flow reserve (CFR), i.e. the ratio of the blood flow in resting and hyperaemic state, e.g. when induced by acetylcholine challenge, i.e. increased blood flow that is artificially induced in the context of these measurements. CFR quantifies the ability of the coronary circulation to augment myocardial blood flow in response to an increased demand for oxygen and nutrients. CFR is affected by the endothelial dysfunction in the coronary arteries as well as in the vessels of the myocardial microcirculation. A high FFR and high CFR are measured in healthy subjects. A low FFR accompanied by a low CFR indicates a significant stenosis, while a high FFR accompanied by a low CFR is an indication of a microvascular disease.

Most commonly, blood flow rate measurements are performed using a sensor-tipped ultrasound Doppler guidewire. With this method the local blood velocity is measured in the direction of ultrasound beam propagation and needs additional geometry information or assumptions about vessel geometry and hemodynamics (e.g. circular cross-section with fully-developed laminar flow profiles) to assess the flow rate. Alternative methods for blood flow rate measurements are thermodilution and hot film anemometry. In thermodilution an infusion catheter is used to administer a bolus of saline at room temperature in the coronary artery. This cold solution will lower the temperature distal to the infusion catheter, which can be sensed by a temperature sensitive pressure guidewire. In hot film anemometry a film is heated by electrical current. On the other hand, the film is cooled by the blood flow. The temperature of the film is determined by measuring the ohmic resistance of the film. Given the electrical input power and the heat capacity of blood, the flow rate can be evaluated from the steady state temperature of the film. Both hot film anemometry as well as thermodilution are a quantifier for flow rate and can be combined with a pressure wire for FFR. They are, however, single point measurements.

GB 2 308 888 A describes a hollow needle with a fiber optic cable for monitoring blood pressure. Pressure and pressure variations cause compression of the fiber optic cable, the resulting strain causing a modification of the Bragg wavelength of a grating written into the fiber optic cable. Pressure measurement is achieved by monitoring the wavelength of light reflected back from the grating in a measurement system. The hollow needle may comprise a catheter or a hypodermic needle. A glass sphere may be incorporated at the end of the fiber optic cable. Deformation of the sphere caused by pressure variations may exert pressure on a grating written in the cable. Alternatively, the surface of the sphere may form an interferometer for measuring pressure variations and a grating may be found in the fiber to allow temperature measurements also to be made. However, the sensitivity of Bragg gratings to hydrostatic pressure is very low, and thus such system may not be able to detect small pressure drops caused by partial occlusions of an artery. Still further, the method is single point and thus requires pullback of the needle to map the pressure variation in a length of an artery.

SUMMARY OF THE INVENTION

It would be advantageous to provide a system and a method for minimally-invasive measurement of blood pressure in an artery, e.g. for detecting stenotic regions of the artery, which is easy to perform and which allows fast mapping of pressure variations in a length of an artery.

In a first aspect, the invention provides a medical system for interventional measurement of blood flow in an artery, the medical system comprising an interventional device comprising at least one optical fiber comprising a plurality of temperature-sensitive optical sensor segments spatially distributed along its longitudinal extension, wherein the interventional device is configured for insertion into an artery such that the optical fiber can be positioned inside the artery and be in thermal contact with blood flowing in the artery, and such that the longitudinal extension of the optical fiber follows a longitudinal extension of the artery, wherein the interventional device comprises a temperature changer arranged to introduce a local change in temperature of a bolus of blood in the artery at a position upstream from one end of the optical fiber, a measurement unit arranged for operational connection to the interventional device, wherein the measurement unit comprises a light source for delivering light to the optical fiber in the interventional device, and wherein the measurement unit is arranged to receive light reflected from the optical fiber and to generate a corresponding time varying output signal, and a processor unit for operational connection to the measurement unit, wherein the processor unit is arranged to run a first processing algorithm so as to translate the time varying output signal from the measurement unit into a set of temperatures corresponding to temperatures at respective positions along the optical fiber, and wherein the processor unit is arranged to run a second processing algorithm arranged to calculate a measure of blood flow at respective positions along the optical fiber in accordance with a temporal behavior of said set of temperatures.

With such system it is possible to measure spatially distributed and time-resolved flow interrogation that allows for simultaneous quantification of flow at multiple locations along an interventional device inside an artery in real-time. Thus, such multi-point flow measurements can be used to find functionally-significant pressure drops across tight stenoses, e.g. as done using FFR. The system is based on the insight that optical sensing can be used to exploit spatially distributed and temporally resolved nature of optical frequency domain reflectometry methods. The advantages of optical sensing in this context are that it eliminates the need for contrast injections or for imprecise and time consuming methods requiring pullbacks of the interventional part in the artery. Still further, unlike Doppler flow wires that interrogate flow tangent to a single/fixed ultrasound beam orientation, this invention would allow for characterization of flow along the entire centerline path followed by the optical fiber. As sensing is performed without electrical connections, the system can be designed in versions which are compatible with MR-guided interventions. Furthermore, the optical fiber based sensor has an extremely small physical footprint and therefore can be deployed within narrow gauge guidewires that minimize the level of hemodynamic flow distortion caused by the flow measurement device itself. This will further allow detection of stenotic regions in more narrow arteries than prior art systems. A still further advantage is that the interventional device part of the system can be manufactured in a low-cost version which is then connected to the measurement unit by a simple optical interface, since the optical fiber is easy to manufacture in thin versions suitable for integration into an interventional guidewire. This allows for the interventional device to be easily replaced and thus the interventional device may be a consumable and manufactured for one-time use thus eliminating the need for sterilization etc. Still further, the system allows for estimation of volume flow rate, average flow velocities along a vessel segment, and estimated pressure drops across (multiple) stenoses, in particular, when flow estimates are combined with intraprocedural quantitative coronary angiography.

Altogether, such a system can improve the speed and efficiency of a wide variety of existing clinical procedures, and could enable even patients with poor renal function to undergo minimally-invasive interventions.

It is understood that the system may include further elements arranged to process the obtained measure of blood flow, e.g. the measure of blood flow versus position may be displayed at a display screen, thus allowing medically skilled persons to perform a diagnosis based thereon.

In preferred embodiments, the measurement unit comprises an interferometer, which allows the possibility of obtaining a precise flow measurement at a good spatial resolution when combined with a light source providing light with a waveguide varying over time, i.e. a swept light source, e.g. based on a laser light source.

Some embodiments comprise a temperature control unit arranged to temporally control a temperature changing effect of the temperature changer, so as to allow temporal tracking of temperature along the optical fiber when the bolus when carried by the blood flow along the artery and thus also along the optical fiber. In a special embodiment, the temperature control unit is arranged to control the temperature changer so as to provide a modulation of cooling or heating of the local bolus of blood at a constant frequency, and wherein the measurement unit is arranged to measure a spatially distributed temperature at said frequency.

In some embodiment, the temperature changer comprises a temperature changing element arranged for thermal contact with blood in the artery, wherein the temperature changing element is arranged to cool or heat a local bolus of blood. This may be in the form of an electrically powered cooling or heating element placed upstream from a distal tip of the optical fiber. In other embodiments, the temperature changer comprises a catheter arranged for injection of a temporally limited bolus of liquid with a temperature different from a temperature of blood in the artery.

In preferred embodiments, the plurality of temperature-sensitive optical sensor segments are Fiber Bragg Gratings or Rayleigh based sensor segments, however other types of temperature-sensitive optical sensor segments may be used.

In some embodiments, the interventional device comprises a guidewire in which the at least one optical fiber is arranged, e.g. the guidewire may be implemented with the optical fiber in the centre, wherein the optical fiber is encircled by a thermally conductive layer, and wherein the optical fiber and the thermally conductive layer are placed in a metal tube so as to provide an appropriate stiffness of the guidewire.

The light source may comprise a laser light source, especially it may be preferred that the light source is arranged to provide light at different wavelengths, e.g. controlled so as to provide a wavelength or frequency swept light signal. In one embodiment, the light from the light source is split into a first part delivered to the optical fiber in the interventional device and into a second part applied to a wavelength measurement unit arranged to determine a measure or wavelength of the light from the light source. Especially, the wavelength measurement unit may comprise a gas cell with a known optical absorption spectrum, and a Mach Zehnder interferometer. Such embodiments can provide a high accuracy in the resulting blood flow measurement, both with respect to spatial position resolution and with respect to flow resolution at each position.

The first processing algorithm may comprise spatially resolving the output signal as a function of time from the measurement unit into a distributed temperature profile by means of Fourier analysis. Thus, such algorithm can be implemented using well-known algorithm components which can run on standard processing equipment in real-time.

The interventional device and the measurement unit may be arranged for interconnection by means of an optical interface so as to allow the measurement unit and the interventional device to be spatially separated during normal use. Standard optical cables and connectors may be used, thus allowing easy replacement of the interventional device in versions where it is manufactured in a low cost version and considered as a disposable element.

To allow MR scanning compatibility, the interventional device is preferably made purely of non-magnetic materials.

The method may further comprise graphical presentation means for visualizing the measured blood flow versus position in the artery, e.g. including a display for presentation of a graph illustrating blood flow versus artery length position. E.g. the measured blood flow data may be displayed overlaid a sketch or an x-ray photo of the relevant artery so as to visualize the obtained data for a medical doctor. The processor unit may be arranged to directly drive a display screen, or the processor unit may be arranged to communicate the measured blood flow data by means of a wired or wireless connection to a computer system with display means. Based on the blood flow data obtained with the system, a medical doctor or other trained personnel may diagnose accordingly.

In a second aspect, the invention provides a method for minimally-invasive measurement of blood flow in an artery, the method comprising an interventional device comprising at least one optical fiber comprising a plurality of temperature-sensitive optical sensor segments spatially distributed along its longitudinal extension, wherein the interventional device comprises a temperature changer, inserting the interventional device into an artery such that the optical fiber can be positioned inside the artery and be in thermal contact with blood flowing in the artery, and such that the longitudinal extension of the optical fiber follows a longitudinal extension of the artery, introducing a local change in temperature of a bolus of blood in the artery at a position upstream from one end of the optical fiber by means of the temperature changer, delivering light to the optical fiber in the interventional device, receiving light reflected from the optical fiber, translating the time varying reflected light into a set of temperatures corresponding to temperatures at respective positions along the optical fiber, and calculating a measure of blood flow at respective positions along the optical fiber in accordance with a temporal behavior of said set of temperatures.

The method is suited for being performed by skilled persons, but does not necessarily need to be performed by medical doctors. The resulting data can be provided to a medical doctor who can diagnose the patient accordingly. E.g. the method may include graphically presenting the measurement data, e.g. by visualizing the data overlaid an x-ray of the artery that has been investigated so as to point out positions of possible stenotic regions.

In some embodiments, temperature calibration measurements from the interventional device are performed to obtain a baseline reference prior to introducing the change in temperature of the local bolus of blood.

In some embodiments, dynamic temperature measurements are performed just before introducing the change in temperature of the local bolus of blood, and measurements are then performed at multiple time points afterwards.

It is appreciated that the same advantages and embodiments of the first aspect apply as well for the second aspect. In general the first and second aspects may be combined and coupled in any way possible within the scope of the invention. These and other aspects, features and/or advantages of the invention will be apparent from and elucidated with reference to the embodiments described hereinafter.

The invention may be implemented in several ways. In some implementations the system is a stand-alone system, e.g. a mobile system including a display screen to visualize the measured data, such as known e.g. for medical ultrasound scanner equipment. In other implementations, the system is purely a measurement tool, and thus the processor unit of the system comprises a wired or wireless interface to communicate measured data, e.g. to a computer system of a hospital or clinic.

BRIEF DESCRIPTION OF THE DRAWINGS

Embodiments of the invention will be described, by way of example only, with reference to the drawings, in which.

DESCRIPTION OF EMBODIMENTS

Figure 1:
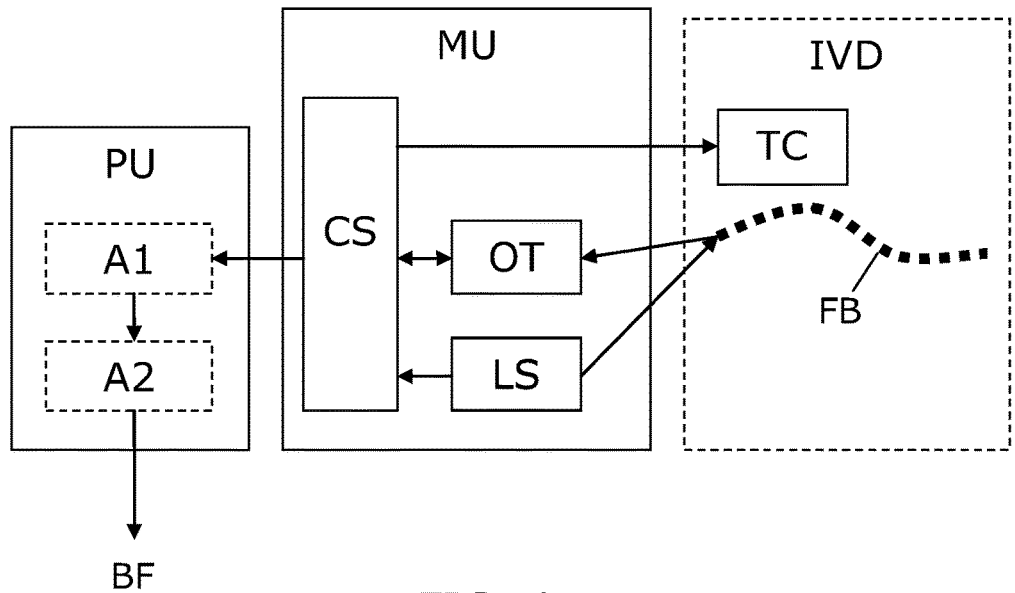
FIG. 1 shows a block diagram of an embodiment of the invention.

FIG. 1 illustrates a block diagram of elements of one medical system embodiment. An interventional device IVD comprises a guidewire with an integrated fiber FB of spatially distributed Fiber Bragg Gratings known in the art. E.g. the fiber has a length of such as 1-2 m. Further, a temperature changer TC is arranged in connection with the guidewire to allow a temporally controlled cooling or heating of a local bolus of blood upstream from the fiber FB. E.g. the temperature changer TC may be in the form of a catheter connected to a container and a device which can deliver a portion of liquid of a specified temperature different from the blood in the artery. In other versions, the temperature changer is an electrically controlled miniature heater which can be controlled to provide temporally limited local heating of a bolus of blood in the artery, e.g. the heater may be controlled to provide heating at a constant modulation frequency. The local heating or cooling introduced by the temperature changer TC allows tracking of the temperature change in the blood flow in the artery along the fiber FB. The guidewire is preferably configured such that it so thin that it can be inserted in an artery without significantly interfering with the blood flow therein.

A measurement unit MU is connected to the interventional device IVD, e.g. via a cable to allow the measurement unit MU to be remotely placed from the patient under examination. Such interconnecting cable is preferably configured with a connector to the interventional device IVD, so as to allow easy replacement of the interventional device which can be manufactured in low cost versions to allow one-time use. The measurement unit MU is optically connected to the fiber FB of the interventional device IVD. A laser light source LS generates light to be applied to one end of the fiber FB, typically to the end of the fiber FB being placed upstream in the blood flow. The light from the same end of the fiber FB, i.e. the light reflected from the Bragg Gratings in the fiber FB, is received by an optical transducer system OT in the measurement unit. A control system CS serves to control the laser light source LS and the optical transducer system OT and comprises optical elements arranged to extract two dimensional temperature data, namely corresponding to temperature versus spatial position along the fiber versus time. Preferably, the control system comprises an implementation of an interferometer, such as known in the art.

The two dimensional temperature data generated by the measurement unit MU are then applied to a processor unit PU, either in wired or wireless form, and the processor unit PU comprises a processor running a first algorithm A1 that translates the time varying output signal from the measurement unit MU into a set of temperatures corresponding to temperatures at respective positions along the fiber FB. This result is then applied to a second algorithm A2 which calculates a measure of blood flow BF at respective positions along the fiber FB in accordance with a temporal behavior of said set of temperatures. This measure of blood flow BF versus position of the fiber FB can be further processed and/or displayed to allow medical personnel to diagnose the patient under examination accordingly.

It is to be understood that the system may be implemented in stand-alone devices including both measurement unit MU and processor unit PU and possibly also a display screen and user interface in one single portable unit. In other versions, only the measurement unit MU is provided as a portable stand-alone device, while the function of the processor unit PU is implemented by a remotely located computer system.

Figure 2:
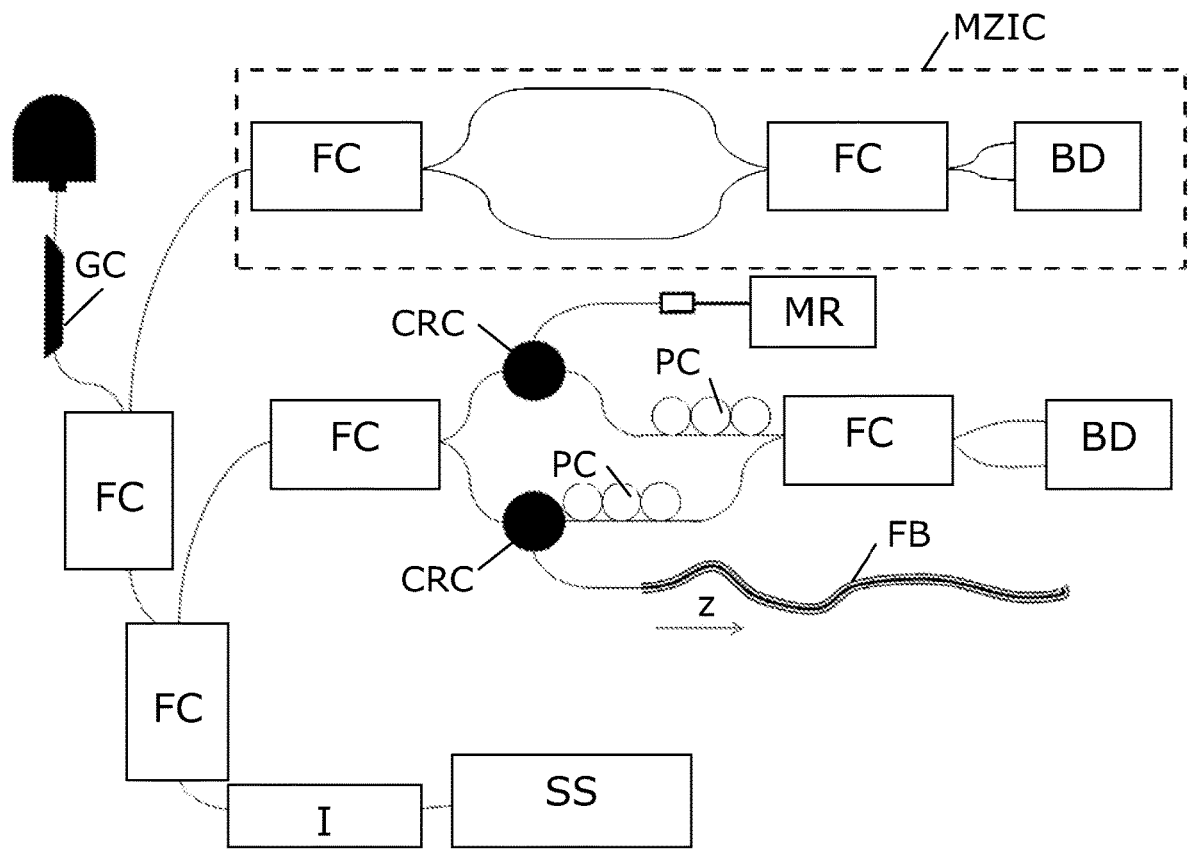
FIG. 2 illustrates elements of another embodiment.

FIG. 2 illustrates an embodiment of the measurement unit in more detail; again the interventional device is based on an optical fiber FB with Fiber Bragg Gratings (FBGs). The fundamental principle behind the operation of a Fiber Bragg Grating (FBG) is Fresnel reflection at each of the interfaces where the refractive index changes. For some wavelengths, the reflected light of the various periods is in phase with one another so that constructive interference exists for reflection and consequently, destructive interference for transmission. The Bragg wavelength is sensitive to strain as well as to temperature. This means that Bragg gratings can be used as sensing elements in fiber optical sensors. In an FBG sensor, the measurand (e.g. temperature) causes a shift in the Bragg wavelength. In the regime of telecommunication wavelengths, the sensitivity is about 13 pm/K. Given the fact that wavelength shifts of about 0.5 pm can routinely by determined, the temperature accuracy is better than 0.1° C.

The optical fiber FB can be incorporated within a guidewire, which can either be used in conjunction with a dilution catheter or can have a miniature fluid channel incorporated into the device to allow for bolus injections of fluid. Via the catheter a small bolus of cold saline is injected. The temperature along the guide wire is measured as a function of time. From the spatially and temporally resolved temperature profile the blood flow rate (similarly as with thermodilution) and the blood flow velocity can be deduced.

The temperature distribution along the fiber FB, direction z, can be obtained with a high spatial resolution by employing an interferometric measurement technique of which an example is depicted in FIG. 2. The optical element shown include balance detectors BD, fiber couplers FC, polarization controls PC, circulators CRC, as well as a mirror MR. Light from a swept source laser system SS is sent through an optical isolator I to prevent back reflections and is split in two fractions. A small fraction is used to monitor the wavelength of the optical source SS by means of a gas cell GC and a Mach Zehnder interferometer with a clock system MZIC. The gas cell GC has a known and calibrated absorption spectrum. The Mach Zehnder interferometer gives a high frequency output signal dependent on the amount of unbalance in its two arms and serves as a trigger signal for the data acquisition system (not shown in FIG. 2). The major part of the light from the swept source SS is directed towards the main interferometer, where it is split in a part that goes to the reference arm with a high reflecting mirror and in a part that goes to fiber FB with the Bragg gratings. The reflected light of both arms is combined in a 2×2 combiner/splitter. Its AC output signals are 180° out of phase, consequently the difference as measured by the balanced receiver does not contain DC signals. The light from the fiber FB has travelled an optical path length depending on the position of the reflecting element along the fiber FB, i.e. in direction z. Consequently, each position z in the fiber FB has a different path length difference with respect to the reference arm mirror MR. While scanning the wavelength each position z will give rise to a signal which varies in time with its own frequency. By Fourier analysis the frequency components can be disentangled, thereby enabling spatially resolved measurement of the wavelength shift, i.e. a distributed temperature profile along the fiber FB.

Figure 3:
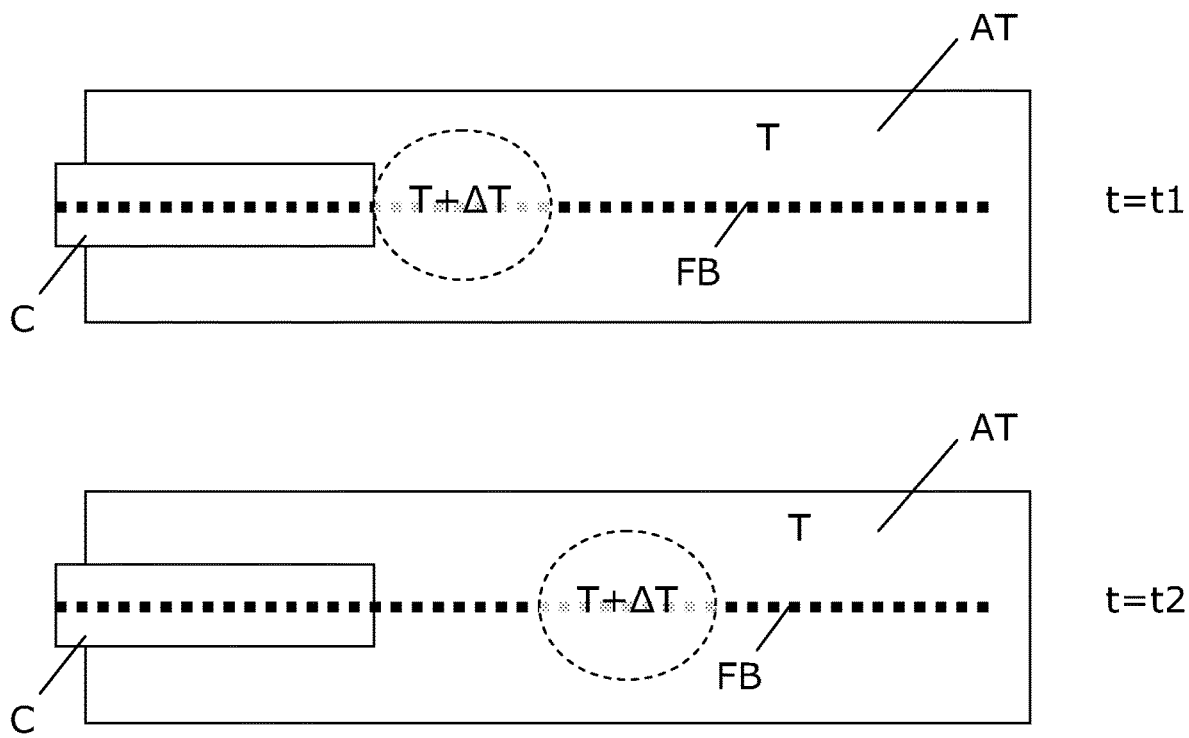
FIG. 3 illustrates a temperature changer implementation comprising a catheter arranged for injection of a bolus of liquid.

FIG. 3 illustrates a system according to one embodiment, Embodiment 1, e.g. for combination with the measurement embodiment illustrated in FIG. 2. A guidewire with an integrated fiber FB containing distributed FBGs is inserted into an artery AT, i.e. into the blood stream, together with a catheter C. The catheter C has an integrated multimode fiber that delivers laser light to blood surrounding the tip during a short time interval. The light is absorbed by blood and increases the temperature at time t=t1, producing a bolus of blood with a slightly elevated temperature T+ΔT, where T is the normal temperature of blood (typically at core body temperature: ~37 degrees ° C.). The bolus propagates rapidly down the artery AT with blood flow, and as illustrated at a later time t=t2, the bolus of blood with elevated temperature has travel in the direction of blood. As it propagates, it contacts different locations along the guidewire and thus along the fiber FB, each of which experiences transient increases in temperature at different time points. These transients in temperature are conducted rapidly to the optical fiber containing the distributed FBGs.

The transient differences in temperature result in localized changes in length along the guidewire and thus along the fiber FB that give rise to very small but detectable differences in the characteristics of the optical light reflected from the optical fiber FB. A processing algorithm, e.g. as known in prior art, is used to translate optical reflectance measurements from the console to distributed temperature measurements (temperature as a function of length along the fiber FB). Preferably, the reflectance measurements are performed interferometrically, e.g. with a system as illustrated in FIG. 2.

Figure 4:
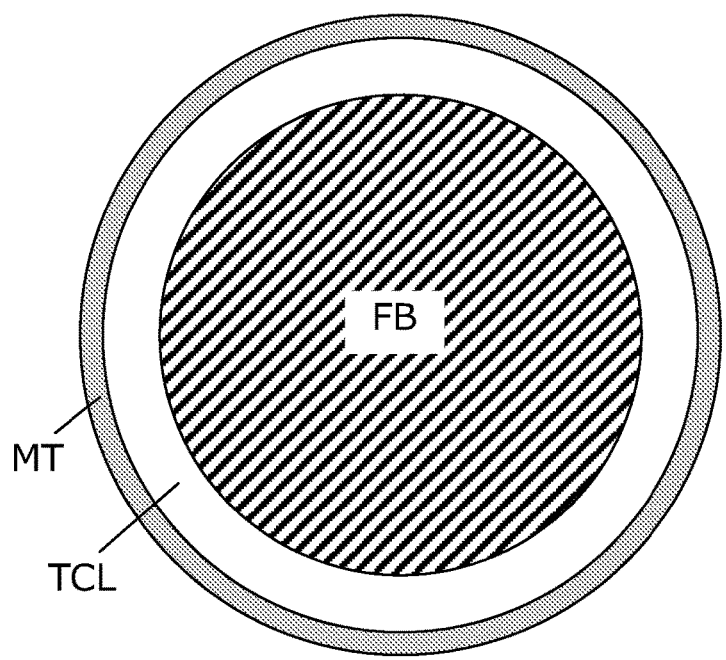
FIG. 4 illustrates implementation of a temperature-sensitive optical fiber arranged inside an interventional guidewire.

FIG. 4 illustrates an example of how an optical fiber FB can be integrated into a guidewire, namely with the fiber FB in the center, and with an intermediate layer TCL of thermally conductive material placed inside a metal tube MT.

Alternatively, the guidewire could consist solely of an optical fiber. Optionally, there could be a metallic coating applied directly to the fiber, with the metallic coating providing mechanical strength. Alternatively, the optical fiber with distributed FBGs could be positioned immediately adjacent to the guidewire. Preferably, it would be attached to the guidewire at multiple points or continuously along its length.

In order to obtain precise blood flow measurements, the system is preferably calibrated according to a calibration procedure. Such calibration of optical measurements from the fiber sensor is performed at a baseline state once the interventional device has been positioned at the target site of interest within the vessel and prior to any temperature challenge. This would establish the baseline geometry configuration as well as the baseline temperature to which the fiber sensor is exposed. Ideally, the calibration measurement is also established in a fashion that is gated to any periodic motion e.g. with ECG or respiratory gating. All further measurements would then be ensured to have arisen from the bolus injection and hemodynamic flow rather than any other physioanatomical changes.

Figure 5:
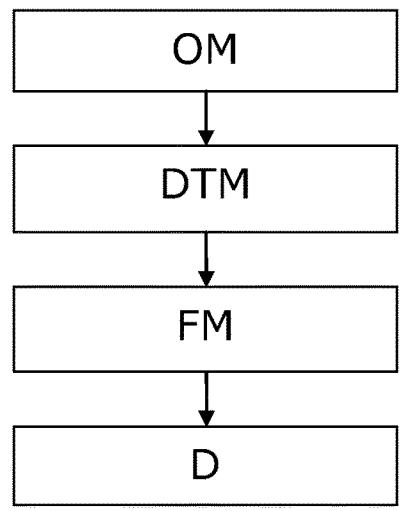
FIGS. 5 and 6 illustrate block diagrams of methods according to the invention.

FIG. 5 illustrates the processing scheme for Embodiment 1 for obtaining distributed flow measurements from distributed temperature measurements. The scheme involves optical measurements OM, distributed temperature measurements DTM, flow measurements FM, and finally displaying D of the results, e.g. as an overlay with a fluoroscopy obtained for the regions of interest.

The processing may involve:
a) tracking the temperature profile as a function of length for a given point in time, and/or
b) tracking the temperature profile as a function of time for a given position.

Administering a heat bolus during a relatively long time period, will give rise to a steady state situation. By following the steady state temperature profile downstream, the flow rate can be determined similarly to the standard thermodilution method. Administering a short heat bolus and measuring the front of the temperature profile one obtains the flow velocity. Changes of the flow velocity as a function of position reveal the position of possible occlusions. Preferably, the creation of the bolus is gated to the cardiac cycle (e.g. using ECG signals) to ensure that the boluses follow similar trajectories each time. Multiple boluses can be performed to derive multiple flow measurements, which can be averaged to increase accuracy.

Embodiment 2 provides an alternative method of administering a thermal bolus in an optical way is by adding a long period Bragg grating (LPG) proximal to the distributed Fiber Bragg gratings and adding a metal coating to the fiber at that position. With a LPG light can be coupled to cladding modes and will consequently be absorbed in the metal, thereby heating the structure locally. An example of such a implementation can be found in P. Caldas et al. *"Fibre Optic Hot-Wire Flowmeter based on a Metallic Coated Hybrid LPG-FBG Structure"*, Proceedings of the European Workshop on Optical Fiber Sensors (Porto, 2010) SPIE Vol. 7653, p. 132.

Embodiment 3 provides the same system as Embodiment 1, except that the bolus of blood with an elevated temperature is created with a non-optical (e.g. electric) heating element integrated in the catheter, or in a similar device that can be inserted through a catheter. Care must be taken not to increase the temperature too much otherwise the heated blood might coagulate. Instead of heating one could also use cooling by administering a cold saline bolus (room temperature). For thermodilution the injection rate is on the order of 20 ml/min, which is only a fraction of the flow rate in the coronary.

Embodiment 4 provides the same system as Embodiment 1, except that a bolus of blood with an elevated temperature is created by the delivery of laser light that is delivered in the fiber with distributed FBGs. Preferably, the light is delivered in the cladding of the fiber (e.g. with a dual-clad fiber), so as not to disturb the optical path the interrogates the FBGs.

Embodiment 5 provides the same system as Embodiment 1, except that additional optical fibers are incorporated into the guidewire or catheter to allow for shape tracking in addition to temperature tracking. The shape tracking information is used to display flow measurement information, e.g. superimposed on fluoroscopic images. Non-optical shape and position tracking can be performed as well (e.g. with EM sensors). The shape tracking information could potentially also be used in the case that multiple boluses are performed to derive multiple flow measurements for averaging, to co-register the spatial locations of the guidewire/catheter in the artery at each measurement.

Embodiment 6 provides the same system as Embodiment 1, except that the algorithm that derives flow measurements from distributed temperature measurements incorporates anatomical information from pre-procedural and/or intra-procedural images. Segmentation of these images could allow for estimates of heat conduction properties of local tissues to be obtained (e.g. with a look-up table). Intravascular Ultra Sound (IVUS) is an example of a technique yielding intra-procedural images. In fact, IVUS and the flow measurement technique of this invention can be combined in one and the same device by adding the optical fiber of one of Embodiments 1-5 to the IVUS catheter.

Embodiment 7 provides the same system as Embodiment 1, except that Rayleigh scattering is used in place of FBGs. The measurement principle is the same. Rayleigh scattering arises from random distribution of small refractive index changes. These variations can be viewed as random Bragg periods. The difference is the ease of fabrication with the associated cost effectiveness at the expense of signal strength.

Embodiment 8 provides the system as one of Embodiments 1-7, where the catheter or guidewire is directed upstream. In this case the bolus should be created at the distal end.

Embodiment 9 provides the system of one of Embodiment 1-5 or 7-8, where the FBGs are chirped in a monotonous way. This means that the resonance wavelength is position dependent. Without temperature changes, the wavelength of reflection is a direct measurement of the position. By continuous measurement of the reflection spectrum using a straightforward and very cost effective optical system (a Light Emitting Diode, small monochromator and multi element detector) the temperature distribution can be monitored in time.

Embodiment 10 provides the same system of any of the previous embodiments Embodiment 1-9, in which a pressure sensing element is added to the tip of the guidewire or catheter. This allows for a combination of volume flow rate, flow velocity and pressure measurement at the same time, but requires pull back in order to obtain pressure gradients.

The following can be seen as an appendix to the described embodiments explaining a simple description of coronary blood flow, and calculations regarding of the method and system of the invention.

A simple description of coronary blood flow will be given by explaining the relation between the various parameters of fluid flow, viz. the flow rate, the flow velocity and pressure gradient. For laminar viscous flow in a tube the flow rate can be described by an Ohmic like description, Darcy's law:

$$Q = \frac{\Delta p}{R}$$

Here, Q is the flow rate (volume per unit of time), $\Delta p$ is the change in pressure over the length of the tube and R is the flow resistance, which is given by the Hagen Poiseuille equation:

$$R = \frac{8\eta l}{\pi a^4}$$

Here, l is the length of the tube, a is the radius and $\eta$ is the viscosity. The velocity exhibits a parabolic profile across the diameter of the tube. Near the boundary the velocity is zero and at the center the velocity is at its maximum. We will use the average flow velocity:

$$\bar{v} = \frac{Q}{\pi a^2} = \frac{a^2 \Delta p}{8\eta l}$$

Typical values for the various parameters in the coronary arteries are given in the Table below. Significant pressure drops across an occlusion are on the order of 20%-30%, i.e. about 3 kPa. Assuming a length of the occlusion of about 1 cm, this would mean the pressure gradient due to the stenosis has increased to 300 kPa/m, which is 200 times the average value. Since, the flow rate before, in and after the occlusion is the same (assuming there are no sidebranch vessels within the length of the stenosis), the change in pressure gradient is solely due to the change in flow resistance caused by a change in cross section. According to the Hagen Poiseuille equation a factor of 200 in pressure gradient relates to a factor of 3.8 in the radius of the tube, and thus a factor of sqrt(200)=14 in flow velocity. Thus, by measuring the flow velocity at multiple points along an artery and monitoring large changes as would be expected within a tight stenosis, a good alternative method is developed for FFR in which pressure differences are measured.

| Quantity | Symbol | Value | Unit |
| --- | --- | --- | --- |
| Flow rate | Q | 120 | ml/min |
| Pressure gradient | $\Delta p/l$ | 1.5 | kPa/m |
| Radius | a | 1.8 | Mm |
| Viscosity | $\eta$ | $3 \cdot 10^{-3}$ | Pa·s |
| Radially averaged velocity | v | 0.2 | m/s |
| Time averaged pressure | <p> | 13 | kPa |

In the above we have assumed that the blood vessels have a circular symmetry also in the areas with an occlusion. This is one extreme case for the geometry. The other extreme is to consider the vessel as being rectangular where the width, w, is much larger than the height, h. In the latter case the flow resistance equals:

$$R_{rect} = \frac{12\eta l}{wh^3}$$

Consequently, the average flow velocity for a rectangular pipe equals:

$$\overline{v_{rect}} = \frac{Q}{wh} = \frac{h^2 \Delta p}{12\eta l}$$

In this case an increase in the pressure gradient by a factor 200 would signify a height change of a factor of 5.8 and the average flow velocity will change by the same amount. In practice the change in average flow velocity going from normal to occlusion will exhibit a behavior between linear (rectangular pipe) and quadratic (circular pipe) dependence.

It should be stressed that the above is a simplified model for coronary flow. The aortic pressure varies during a heart beat cycle from 16 kPa in systole to 10 kPa in diastole. The flow in the coronary arteries is at its maximum in the diastole owing to the contraction of the left ventricle. Furthermore, the diameter of the blood vessels is elastic and therefore not constant during a heart cycle.

Regarding calculations on realizations, the following data can be observed.

| Quantity | Units | Water | Silica |
| --- | --- | --- | --- |
| Heat conductivity, K | mW/cm · K | 6 | 11 |
| Density, $\rho$ | gr/cm3 | 1 | 2.65 |
| heat capacitance, Cv | J/gr · K | 4.2 | 0.84 |
| Thermal diffusivity, D | cm2/s | 0.0014 | 0.0049 |

The exponential decay time of heat over a distance L equals:

$$\tau = \frac{L^2}{\pi^2 D}$$

For a vessel of 3 mm diameter and filled with a water like fluid, the specific decay time of the heat is around 1.5 seconds. This is ample time to get a temperature profile; in other words, any heat absorbed by blood will not have diffused significantly into the surrounding tissue in the time taken for a bolus of blood to traverse a length of 10 cm (assuming a blood speed of 25 cm/s).

The heat capacitance of a fiber with 300 micron diameter and 10 cm length equals 16 mJ/K. This means that the amount of heat in the injection should be much larger than this, say 0.1 J/K. (this corresponds to 0.024 cc of water).

Assuming a blood speed of 25 cm/s and a vessel diameter of 3 mm, 0.024 cc of blood is transported in 14 milliseconds. For a fiber of 0.3 mm diameter, the specific decay time of the heat is around 5 milliseconds. This means that the time taken for the fiber to absorb heat is smaller than the time in which the bolus of blood with higher temperature is in contact with it. Hence, the thermometer that can be implemented according to the invention is fast enough.

When heating a part of the catheter, the amount of energy should equal the rise in temperature by 1 degree of 0.024 cc of water in 0.014 seconds. This corresponds to 0.1 J in 0.014 seconds equaling 7 Watts. This is a reasonable amount of power to deliver optically as well as with electrical methods.

Figure 6:
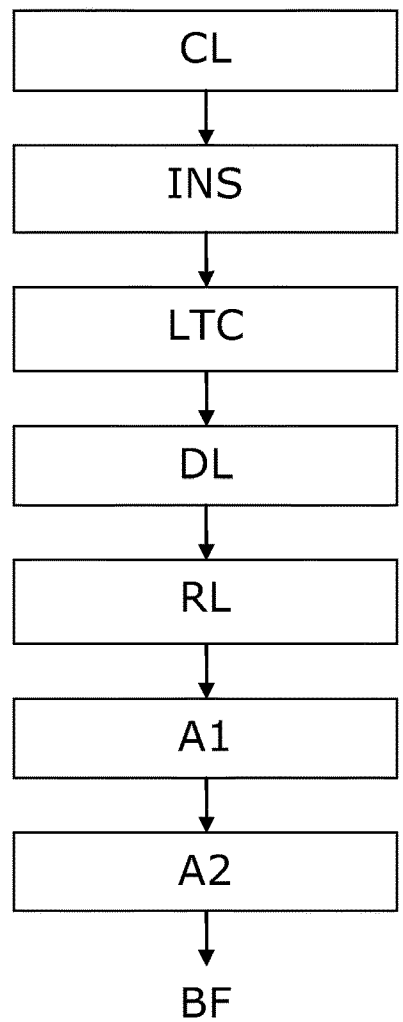

FIG. 6 illustrates in block diagram for a method for minimally-invasive measurement of blood flow in an artery according to an embodiment of the invention with one of the system embodiments described in the foregoing. The method comprises an initial calibration routine CL including performing temperature calibration measurements to obtain a baseline reference prior to a bolus of injection of fluid at a temperature different from the blood, either with a bolus of saline that is cold or hot relative to blood temperature. The interventional device with the optical fiber is then inserted into the artery INS, such that the longitudinal extension of the optical fiber follows a longitudinal extension of the artery. Next, a local change in temperature LTC of a bolus of blood in the artery at a position upstream from one end of the optical fiber by means of the temperature changer is provided. Light DL is being delivered to the optical fiber in the interventional device, and reflected from the optical fiber is received RL. Based on the received light, the time varying reflected light is translated into a set of temperatures corresponding to temperatures at respective positions along the optical fiber using an algorithm A1. Subsequently, a measure of blood flow BF at respective positions along the optical fiber, in accordance with a temporal behavior of said set of temperatures resulting from A1, is calculated using a second algorithm A2.

It is to be understood, that the method may be split into one part where a trained staff, e.g. medical personnel, performs the initial steps CL and INS, i.e. while the remaining part of the method can be seen as a separate method which can be performed exclusively by an apparatus. Thus, once the system has been calibrated and the interventional device has been inserted into the artery of the patient, the remaining method steps are suited for being performed automatically by an apparatus or system as described in the foregoing.

To sum up, the invention provides a medical system for minimally-invasive measurement of blood flow in an artery (AT). An interventional device (IVD) with an optical fiber (FB) comprising a plurality of temperature-sensitive optical sensor segments, e.g. Fiber Bragg Gratings, spatially distributed along its longitudinal extension is configured for insertion into an artery (AT). A temperature changer (TC) is arranged in the IVD to introduce a local change in temperature (ΔT) of a bolus of blood in the artery, to allow thermal tracking over time with the optical fiber (FB). A measurement unit (MU) with a laser light source (LS) delivers light to the optical fiber (FB) and receives light reflected from the optical fiber (FB) and generates a corresponding time varying output signal. A first algorithm (A1) translates this time varying output signal into a set of temperatures corresponding to temperatures at respective positions along the optical fiber (FB). A second algorithm (A2) calculates a measure of blood flow (BF) at respective positions along the optical fiber (FB) in accordance with a temporal behavior of said set of temperatures. Such system can be used to quickly scan an artery for diagnosing stenotic regions without the need for pullbacks or injection of toxic liquids. A good spatial resolution of the blood flow measurement can be obtained in real-time.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical system for interventional measurement of blood flow in an artery, the medical system comprising:
    an interventional device including an optical fiber having a plurality of temperature-sensitive optical sensor segments spatially distributed along a longitudinal extension of the optical fiber,
        wherein the interventional device is configured for insertion into the artery such that the optical fiber can be positioned inside the artery and be in thermal contact with blood flowing in the artery, and such that the longitudinal extension of the optical fiber follows a longitudinal extension of the artery, and
        wherein the interventional device further includes a temperature changer configured to introduce a local change in temperature of a bolus of blood in the artery at a position upstream from one end of the optical fiber;
    a measurement unit arranged for operational connection to the interventional device,
        wherein the measurement unit includes a light source for delivering light that is split into a first part of the light and a second part of the light,
        wherein the first part of the light is delivered to the optical fiber in the interventional device and an interferometer configured to receive light reflected from the plurality of temperature-sensitive optical sensor segments in response to the first part of the light and to generate wavelength data that includes information indicating temperatures at spatial positions of the optical fiber corresponding to the plurality of temperature-sensitive optical sensor segments, and
        wherein the second part of the light is applied to a wavelength measurement unit configured to monitor wavelength of the light from the light source, the wavelength measurement unit comprising a gas cell with a known optical absorption spectrum and a Mach Zehnder interferometer; and
    a processor unit for operational connection to the measurement unit and a non-transitory storage medium for storing instructions that, when executed by the processor unit, cause the processor unit to:
        spatially and temporally extract the temperatures from the wavelength data into a distributed temperature profile of the temperatures at the respective spatial positions of the plurality of temperature-sensitive optical sensor segments along the optical fiber, the distributed temperature profile being responsive to a downstream flow of the bolus of blood over the plurality of temperature-sensitive optical sensor segments; and
        track local transient changes of temperature at the respective spatial positions of the plurality of temperature-sensitive optical sensor segments along the optical fiber in accordance with the temperatures provided in the distributed temperature profile to detect the blood flow in the artery, wherein
        the local transient changes of temperature are tracked as a function of time for a given position of one of the plurality of temperature-sensitive optical sensor segments along the optical fiber.

2. The medical system according to claim 1, wherein the temperature changer is configured to provide a modulation of cooling or heating of the bolus of blood at a constant frequency, and
    wherein the measurement unit is configured to measure a spatially distributed temperature of the plurality of temperature-sensitive optical sensor segments at the constant frequency.

3. The medical system according to claim 1, wherein the temperature changer includes a catheter configured to inject a temporally limited bolus of liquid with a temperature different from a temperature of blood in the artery to introduce the local change in temperature of the bolus of blood in the artery.

4. The medical system according to claim 1,
wherein the temperature changer includes a temperature changing element arranged for thermal contact with blood in the artery, and
wherein the temperature changing element is configured to cool or heat the bolus of blood to introduce the local change in temperature of the bolus of blood in the artery.

5. The medical system according to claim 1, wherein the plurality of temperature-sensitive optical sensor segments includes at least one of: Fiber Bragg Gratings, or Rayleigh based sensor segments.

6. The medical system according to claim 1, wherein the interventional device includes a guidewire in which the optical fiber is arranged.

7. The medical system according to claim 1, wherein the light source includes a laser light source configured to provide light at different wavelengths.

8. The medical system according to claim 1, wherein spatially and temporally extracting the temperatures from the wavelength data into the distributed temperature profile comprises performing a Fourier analysis of wavelength data associated with each of the temperature-sensitive optical sensor segments.

9. The medical system according to claim 1, wherein the interventional device and the measurement unit are arranged for interconnection by means of an optical interface so as to allow the measurement unit and the interventional device to be spatially separated during normal use.

10. The medical system according to claim 1, wherein the interventional device is made of non-magnetic materials.

11. A method for minimally-invasive measurement of blood flow in an artery, the method comprising:
providing an interventional device including an optical fiber having a plurality of temperature-sensitive optical sensor segments spatially distributed along a longitudinal extension of the optical fiber;
inserting the interventional device into the artery such that the optical fiber can be positioned inside the artery and be in thermal contact with blood flowing in the artery, and such that the longitudinal extension of the optical fiber follows a longitudinal extension of the artery;
introducing a local change in temperature of a bolus of blood in the artery at a position upstream from one end of the optical fiber;
splitting light from a light source into a first part of light and a second part;
delivering the first part of light to the optical fiber in the interventional device;
applying the second part of the light for monitoring wavelength of the light from the light source using a gas cell with a known optical absorption spectrum and a Mach Zehnder interferometer;
receiving light reflected from the plurality of temperature-sensitive optical sensor segments in response to the first part of light and generating wavelength data using an interferometer, wherein the wavelength data indicates temperatures at spatial positions of the optical fiber corresponding to the plurality of temperature-sensitive optical sensor segments;
spatially and temporally extracting the temperatures from the wavelength data into a distributed temperature profile of the temperatures at the respective positions of the plurality of temperature-sensitive optical sensor segments along the optical fiber, the distributed temperature profile being responsive to a downstream flow of the bolus of blood over the plurality of temperature-sensitive optical sensor segments; and
tracking local transient changes of temperature at the respective positions of the plurality of temperature-sensitive optical sensor segments along the optical fiber in accordance with the temperatures provided in the distributed temperature profile to detect the blood flow in the artery, wherein
the local transient changes of temperature are tracked as a function of time for a given position of one of the plurality of temperature-sensitive optical sensor segments along the optical fiber.

12. The method according to claim 11, wherein introducing the local change in temperature of the bolus of blood in the artery comprises providing a modulation of cooling or heating of the bolus of blood at a constant frequency, wherein the blood flow in the artery is measured at the constant frequency.

13. The method according to claim 11, wherein introducing the local change in temperature of the bolus of blood in the artery comprises injecting a temporally limited bolus of liquid with a temperature different from a temperature of blood in the artery through a catheter.

14. The method according to claim 11, wherein introducing the local change in temperature of the bolus of blood in the artery comprises cooling or heating the bolus of blood through a temperature changing element in thermal contact with the blood in the artery.

15. The method according to claim 11, wherein the plurality of temperature-sensitive optical sensor segments comprise Fiber Bragg Gratings.

16. The method according to claim 11, wherein the plurality of temperature-sensitive optical sensor segments comprise Rayleigh based sensor segments.

* * * * *